United States Patent
Dixon et al.

(10) Patent No.: US 6,656,181 B2
(45) Date of Patent: *Dec. 2, 2003

(54) METHOD AND DEVICE UTILIZING TAPERED SCREW SHANKS FOR SPINAL STABILIZATION

(76) Inventors: Robert A Dixon, 10577 Durham Pl., Powell, OH (US) 43065; Donald J. Hackman, 3499 Kirkham Rd., Upper Arlington, OH (US) 43221

( * ) Notice: Subject to any disclaimer, the term of this patent is extended or adjusted under 35 U.S.C. 154(b) by 0 days.

This patent is subject to a terminal disclaimer.

(21) Appl. No.: 09/996,858

(22) Filed: Nov. 20, 2001

(65) Prior Publication Data

US 2002/0082603 A1 Jun. 27, 2002

Related U.S. Application Data

(60) Provisional application No. 60/252,676, filed on Nov. 22, 2000.

(51) Int. Cl.[7] .................................................. A61B 17/56
(52) U.S. Cl. .................................................. 606/69
(58) Field of Search ............................. 606/69, 70, 71, 606/61

(56) References Cited

U.S. PATENT DOCUMENTS

| | | | | |
|---|---|---|---|---|
| 2,494,229 A | * | 1/1950 | Collison | 606/73 |
| 3,593,709 A | * | 7/1971 | Halloran | 606/69 |
| 3,798,776 A | * | 3/1974 | Lentine et al. | 32/26 |
| 4,503,848 A | * | 3/1985 | Caspar et al. | 606/69 |
| 5,098,434 A | * | 3/1992 | Serbousek | 606/73 |
| 5,147,361 A | * | 9/1992 | Ojima et al. | 606/61 |
| 5,275,601 A | | 1/1994 | Gogolewski | |
| 5,364,399 A | * | 11/1994 | Lowery et al. | 606/69 |
| 5,520,690 A | * | 5/1996 | Errico et al. | 606/61 |
| 5,522,895 A | | 6/1996 | Mikos | |
| 5,549,612 A | | 8/1996 | Yapp | |
| 5,578,034 A | | 11/1996 | Estes | |
| 5,676,666 A | * | 10/1997 | Oxland et al. | 606/61 |
| 5,681,310 A | * | 10/1997 | Yuan et al. | 606/61 |
| 5,681,311 A | * | 10/1997 | Foley et al. | 606/61 |
| 5,772,662 A | | 6/1998 | Chapman et al. | |
| 5,904,683 A | * | 5/1999 | Pohndorf et al. | 606/61 |
| 6,129,730 A | * | 10/2000 | Bono et al. | 606/73 |
| 6,159,213 A | * | 12/2000 | Rogozinski | 606/70 |
| 6,206,881 B1 | | 3/2001 | Frigg et al. | |
| 6,206,882 B1 | * | 3/2001 | Cohen | 606/69 |
| 6,228,085 B1 | | 5/2001 | Theken et al. | |
| 6,235,033 B1 | * | 5/2001 | Brace et al. | 606/69 |
| 6,269,716 B1 | | 8/2001 | Amis | |
| 6,293,949 B1 | * | 9/2001 | Justis et al. | 606/61 |
| 6,342,055 B1 | * | 1/2002 | Eisermann et al. | 606/69 |
| 6,428,542 B1 | * | 8/2002 | Michelson | 606/70 |
| 6,432,107 B1 | * | 8/2002 | Ferree | 606/61 |
| 6,454,769 B2 | * | 9/2002 | Wagner et al. | 606/69 |
| 2001/0014807 A1 | * | 8/2001 | Wagner et al. | 606/61 |
| 2001/0041894 A1 | * | 11/2001 | Campbell et al. | 606/61 |
| 2002/0004660 A1 | * | 1/2002 | Henniges et al. | 606/69 |
| 2002/0016595 A1 | * | 2/2002 | Michelson | 606/73 |
| 2002/0045897 A1 | * | 4/2002 | Dixon et al. | 606/61 |

FOREIGN PATENT DOCUMENTS

| | | | | |
|---|---|---|---|---|
| EP | 0530585 | | 10/1993 | |
| WO | wo 9426193 | * | 11/1994 | 606/61 |

* cited by examiner

*Primary Examiner*—Eduardo C. Robert
(74) *Attorney, Agent, or Firm*—Scott M. Oldham

(57) ABSTRACT

A method and a device are provided for stabilizing vertebrae in a human spine for the purpose of fixing one vertebra with respect to other vertebrae and with respect to other parts of the spinal column. This device comprises a plate and bone screws fabricated from metals. The bone screw maintains the plate in contact with the vertebrae. A tapered screw head is pulled into a machined tapered hole, locking the screw to the plate. The taper is configured to be self-locking preventing the screw from backing out. The taper may be within the fixed structure of the plate, or within an insert placed into the plate.

16 Claims, 3 Drawing Sheets

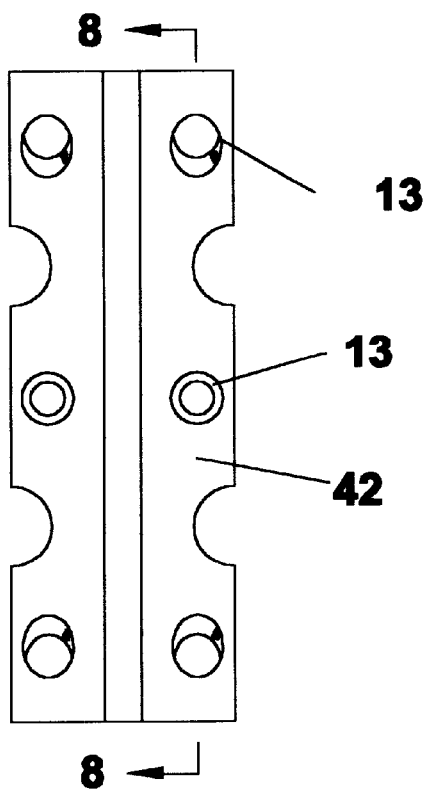
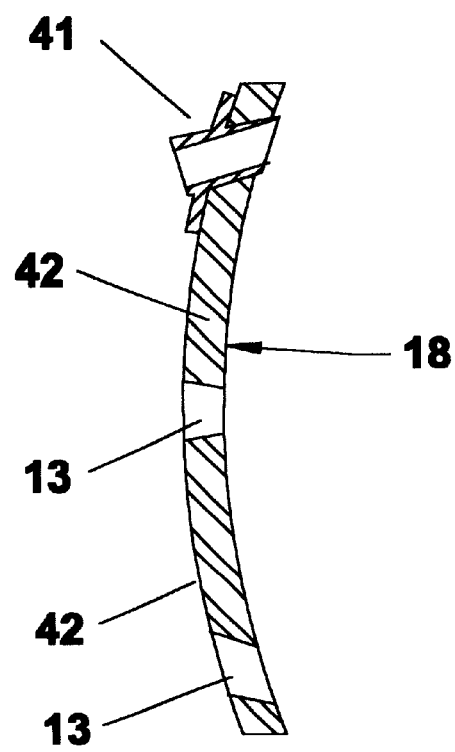
FIG. 7
FIG. 8

METHOD AND DEVICE UTILIZING TAPERED SCREW SHANKS FOR SPINAL STABILIZATION

This application claims the benefit of provisional application No. 60/252,676 filed Nov. 22, 2000.

FIELD OF THE INVENTION

The invention relates generally to implantable medical devices and their methods of use for stabilizing skeletal bone, and relates more particularly to implantable medical devices fabricated of metals and their use for stabilizing the vertebrae of a human spine.

BACKGROUND OF THE INVENTION

With normal anatomy, the vertebrae of the spinal column are held together and to the skeleton by a complex arrangement of ligaments, tendons and muscles. Degenerative diseases, deformities, or trauma may cause abnormal conditions. These problems generally cause or allow displacement or rotation of a vertebra relative to the adjacent vertebra. When spinal discs rupture or bulge the intervertebral space between two adjacent vertebras 31 and 32 can decrease and cause discomfort to the patient. Frequently the bulging does no harm, but if it compresses against the spinal cord or a nerve it may cause pain, loss of sensation, or weakness. When surgery is needed, the discs may be replaced with grafts that will heal or "fuse" the adjacent vertebrae together. This implant, with its associated stabilization, maintains the vertebral position while healing takes place. This is referred to as "spinal fusion". The objective of spinal implants is to facilitate realignment and/or fixation of spinal elements. Clinical studies have demonstrated that surgeries using spinal implants are more effective at maintaining alignment and providing rigidity to the spine than surgeries in which implants are not used. Since the introduction of stabilizers as crude plates, rods, and wires, these devices have been developed into sophisticated appliances, which can be assembled and configured to rigidize spines of any size or condition. These stabilizers provide mechanical fixation for restraint of an implanted graft material. With this fixation, displacement during healing is significantly reduced thereby reducing the failure rate of the fusion surgery.

Prior Technology

The majority of existing spine stabilizers use plates that are bent in both the axial plane to conform to the vertebrae, and along the spinal axes to maintain lordosis. Bicortical screw purchase has been favored because of the increased strength of the construct and increased screw thread area within the bone. These screws are more technically challenging to place and add increased risk of morbidity from neural canal penetration and screw backout. The reduced strength and decreased thread area of a unicortical screw purchase increases the probability of screw back out or loosening resulting in soft tissue organ (e.g. esophageal) injury and loss of rigidization of the fusion construct. Screw back out and loosening has led to the development of mechanisms for locking the screw head to the plate in unicortical screw plate designs. Such locking mechanisms not only prevent screw back out they also reduce the tendency of the screw head to pivot within the plate. These devices contain many intricate components that increase the cost and reduce reliability. The unicortical devices presently available are relatively rigid devices.

U.S. Pat. No. 5,578,034 to Estes discloses a bone screw with an enlarged head and an annular collar surrounding the bone screw shaft. The collar's inner diameter shrinks in response to a change in temperature, trapping the collar between head and the threads of the bone screw.

U.S. Pat. No. 6,269,716 to Amis discloses a tapered screw head for biodegradable medical implants. The screw head has a star shaped outer circumference with external features for rotation. In the disclosed patent the resorbable fastener tapered head is connected to a threaded shaft. The stress raisers of both the threaded portion and tapered head are in the high stressed area at the plate/bone interface. This design is successfully used in non-load bearing bones in facial and cranial surgeries. However it does not have the required strength for load bearing applications.

U.S. Pat. No. 5,549,612 to Yapp discloses an osteosynthesis plate with a locking mechanism that is integral with the plate comprising a rotatable cam adjacent to the screw holes to inhibit movement of the screw.

The following patent is an example of stabilizing systems that disclose or claim tapered screws:

U.S. Pat. No. 6,228,085 to Theken discloses a metallic bone fixation system with a three-dimensionally anatomically contoured plate to fit the anterior lateral profile of the vertebrae and forming a ledge to maintain the space between two vertebrae. The system is designed for use as a metal plate and is suited for thoracic and lumbar spines. It uses setscrews and threads in a portion of the hole. It has irregular surfaces in the plate such as steps, spines or teeth to bite into a bone. Such features are costly. The screw may have a tapered outer surface adjacent to the threaded portion, to provide pullout resistance of the screw in the plate.

Locking Tapers

Locking tapers, sometimes called self locking or self-holding tapers, are tapered round shanks that fit into round sockets with matching taper angles. These tapers are usually less than 5 degrees on a side. During engagement the shanks are firmly seated in the socket by an axial force such as tapping with a hammer or drawing in with a screw thread. These axial forces provide a normal force component that is sufficient to create frictional forces, which will resist relative rotation of the shank with the socket when they are assembled.

Interference Fits

Interference fits between two parts are created by forming the parts so that one or both contacting surfaces yield to create high normal compression forces. These forces provide friction to retain one piece (the male part) in the other piece (the female part) to decrease or eliminate one piece from moving with respect to the other under axial or rotational loading. In the case of cylindrical shafts and cylinder holes, the shaft diameter may be formed slightly larger than the hole diameter. This type of assembly is also called a press fit. The amount of interference is controlled during manufacture and cannot be altered during assembly. If the shaft and hole are manufactured of matching tapers, the assembly force and displacement may control the amount of interference.

The preferred metals for implants are Titanium alloys, especially TiA16V4, because of the decreased interference with magnetic resonant imaging (MRI) techniques used for postoperative evaluation. This is due to minimal ferromagnetic properties which also improve lifestyle considerations when metal detectors come in play. TiA16V4 is a well documented material in clinical use with an excellent safety record and FDA approval.

SUMMARY OF THE INVENTION

The present patent discloses a method and a device for stabilizing vertebrae in a human spine for the purpose of temporarily fixing the vertebra with respect to other vertebrae and with respect to other parts of the spinal column. This device comprises a metallic plate and bone screws fabricated from metals. The plate has a plurality of tapered holes with the smaller diameter end adjacent to the vertebra and the larger diameter on the opposite side of the plate. The bone screw has a threaded portion that engages a predrilled and/or threaded hole in the vertebra or the graft. The bone screw also has a tapered portion with a major diameter greater than the large diameter of the tapered hole. The bone screw maintains the plate in contact with the vertebra. The screw tapered portion is pulled into a matching tapered hole, locking the screw to the plate. The taper is configured to be self-locking, preventing the screw from backing out.

OBJECTS OF THE PRESENT INVENTION

An object of the present invention is to provide a method and a device for a fusion, fixation and/or for spinal stabilization.

Another object of the present invention is to provide a reliable stabilizer device which is effective yet uncomplicated mechanically and simple to manufacture.

Another object of the present invention is to provide a spinal fusion and a spinal stabilization device using metallic stabilization plates and plate attachment devices.

Another object of the present invention is to provide devices and methods for cervical, thoracic, and lumbar spinal fusions anteriorly, posteriorly, and/or laterally.

BRIEF DESCRIPTION OF THE DRAWINGS

The present invention will be understood better from the following detailed description of the preferred embodiment. In the accompanying drawings the reference numbers refer to the individual parts described in the text.

FIG. 7 is a front (proximal) of view of a two level plate.

FIG. 8 is a side section view, at 8—8 of FIG. 7, of a two level plate with a lordordotic curvature showing a guide bushing placed on one of the holes.

DETAILED DESCRIPTION OF THE INVENTION

For simplification the stabilizer system is described as a cervical stabilizer in one of many conceivable embodiments. That is not to imply that this is the only embodiment within which the stabilizing system can be configured. For consistency in this patent the word stabilizer refers to the plate screw assembly, whereas the word graft refers to the material replacing the removed disc or vertebrae. This device comprises a plate and bone screws fabricated from metals, alloys or composite materials.

The Device

Figure 1:
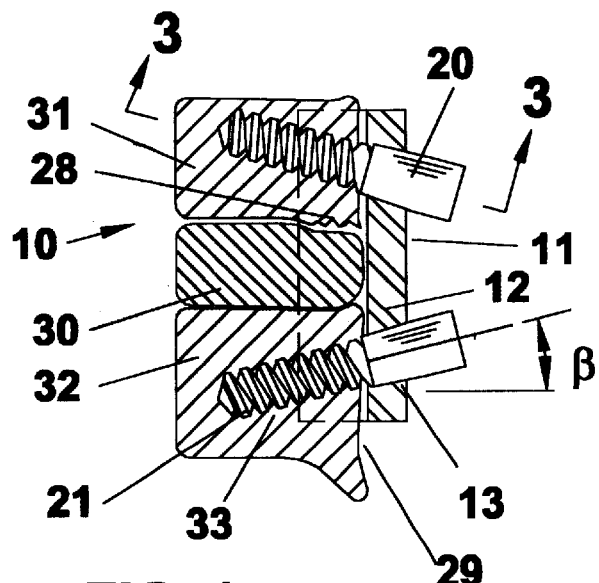
FIG. 1 is a side sectional view, at 1—1 of FIG. 3, of the metallic spinal stabilization system shown implanted on the cervical portion of a human spinal column.
Figure 2:
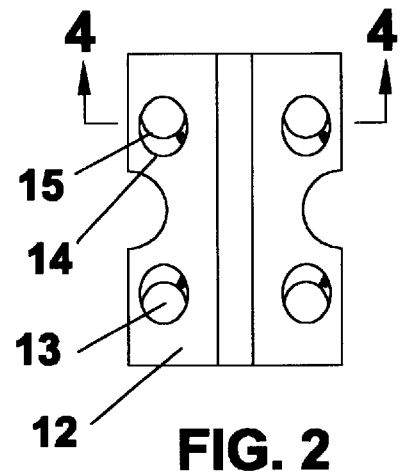
FIG. 2 is a front (proximal) view of the plate
Figure 3:
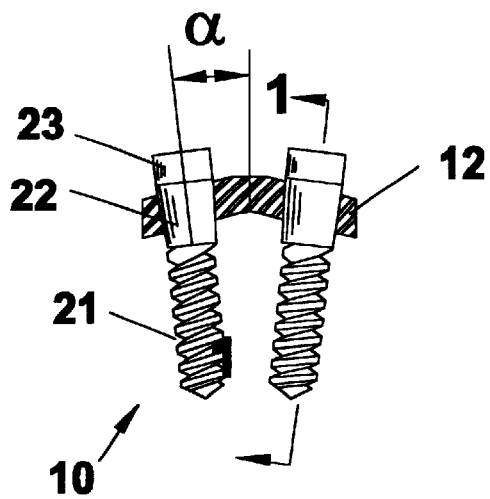
FIG. 3 is a top section view, at 3—3 of FIG. 1, of the metallic spinal stabilization system shown with the vertebrae removed.

Referring to FIGS. 1, 2, and 3 in the preferred embodiment, the system 10 is attached to the anterior surface of the spine 29. The system 10 may be modified for use on the lateral aspects of the spine. The system comprises a plate 12 with holes 13 and bone screws 20. The system 10 and its components are described in detail in the following paragraphs. The bone stabilizing method of implanting is described in "the method" section of this patent.

Referring to FIGS. 1, 2, and 3, in particular, the anterior cervical plate system 10 is shown in combination with bone screws 20. Each of the plate 12 tapered holes 13 receives a bone screw. In the preferred embodiment the plate 12 is fabricated from a single piece of material or from a metal plate with inserts containing two or more tapers or tapered sections or inserts. As described in the "Prior technology" section, these plates contained either threads for locking the screw, or small locking devices such as cams were used to prevent the screws from backing out under sustained or repetitive movement of the patient. These diameters allow the bone screws 20 to be inserted, shank first, into any of screw holes 13 from the anterior side 11 of plate 12, with the threaded shank 21 passing through the hole 13 of the posterior surface. The thread engages a predrilled and prethreaded hole 33 in the vertebra 31 and 32 or the graft 30. The bone screw maintains the plate 12 in contact with the vertebra 31 and 32. The vertebral projection 28 may require removal to allow clearance for the plate 12 and the graft 30. The screw tapered portion 22 is pulled into the matching tapered plate hole 13 locking the screw 20 to the plate 12. The taper is configured to be self-locking, preventing the screw from backing out. There may be one or more tapers within each plate hole 13, or on each screw taper 22 or a plate insert. The screw holes may be placed at an axial angle β to pull the vertebrae together or a radial angle a to give the screws pull out resistance.

The Plate

Referring to FIGS. 1, 2, and 3, the plate 12 is the framework upon which the bone screws 20 are attached. The plate 12 has two holes 13 per vertebra, on a centerline perpendicular to the patient's spinal axis, to receive and contain the bone screws 20. Some materials do not have the yield, tensile, compressive, endurance, or shear strengths required to maintain the clamping force on the small area available for screw threads in a thin plate, and the threads are easily stripped or cross-threaded during installation of the screw lock. The locking tapers, of this patent eliminate the need for plate threads or other complicated locking mechanisms on the plate. Referring to FIGS. 5a, 5b, 6a, 6b, and 6c, in the preferred embodiment, the screw 20 is held in place with two or more locking tapers or tapered sections 16 and 17 in plate 12. The plate and the screws may also have two tapers of different angles 16 and 17, as shown in FIG. 6c. These tapers allow the use of the full thickness of the plate 12 for bending reaction area. Two tapered sections are used to insure that the screw to plate contacts have the widest moment reaction distance and the highest bearing compression stress possible. This wider distance will reduce the tendency of the screw head to pivot within the plate. The high bearing stress provides additional friction to lock the screw.

Figure 4A:
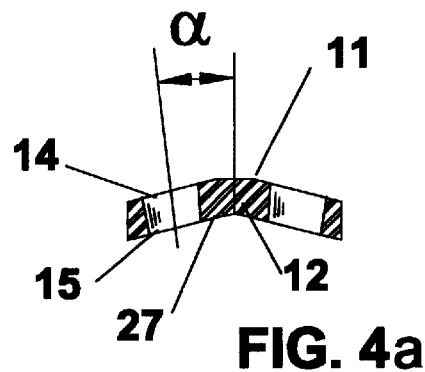
FIG. 4a is a top sectional view, at 4—4 of FIG. 2, of the plate with a "V" shaped posterior side.
Figure 4B:
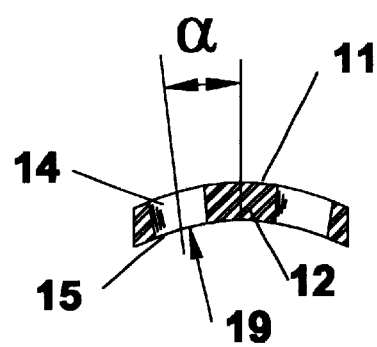
FIG. 4b is a top sectional view, at 4—4 of FIG. 2, of the plate with a curved posterior side.
Figure 5A:
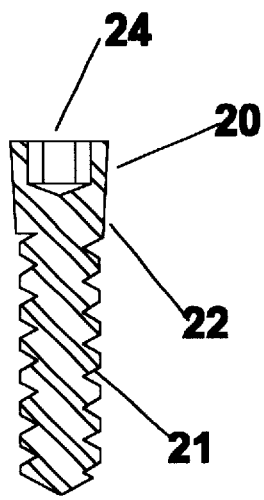
FIG. 5a is an enlarged section view at 5—5, of FIG. 5b of the bone screw with wrench socket.

Referring to FIGS. 4a, 4b and 8 the plate contact surface is made up of one or more flat plane surfaces 27 or one or more curved surfaces 19 shaped to allow for stabilizing the spine or positioning individual vertebra as required. However the surface is not sculptured for individual protrusions or depressions of the vertebral anterior face 29. The radius of curvature 18 in the longitudinal plane is selected to approximate the desired lordosis of the section of the cervical vertebral column to which plate 12 is affixed. The radius of curvature in the transverse plane 19 is selected to conform to the transverse curvature of the anterior surfaces of the cervical vertebrae. The transverse curvature may be in the form of a v-shaped bend, as illustrated in FIG. 4a or a curved surface 19 as illustrated in FIG. 4b. The plate 42 can also be fabricated to stabilize two or more vertebrae levels as shown in FIG. 7 and FIG. 8.

The Bone Screw

Figure 6A:
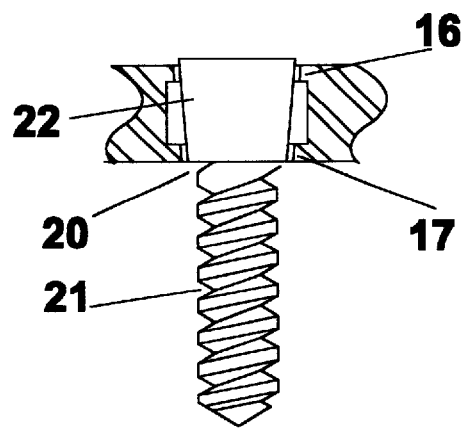
FIG. 6a is an enlarged sectional view, at 6—6 of FIG. 5b, of a bone screw with two separate tapered sections in the plate.
Figure 5B:
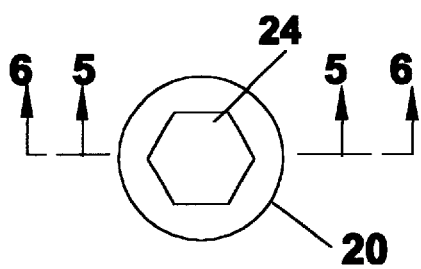
FIG. 5b is an enlarged top view of the bone screw wrench socket in the tapered portion.
Figure 6B:
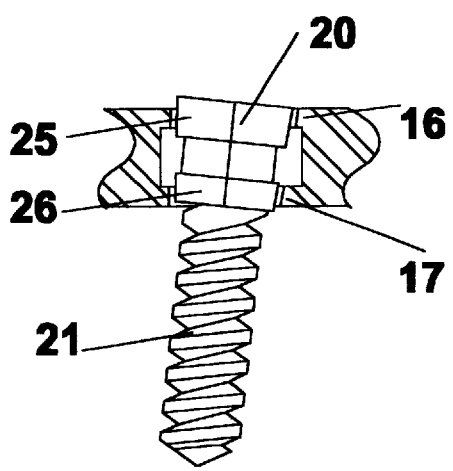
FIG. 6b is a sectional view, at 6—6 of FIG. 5b, of an angled bone screw with two separate tapered sections in both the plate and the screw.
Figure 6C:
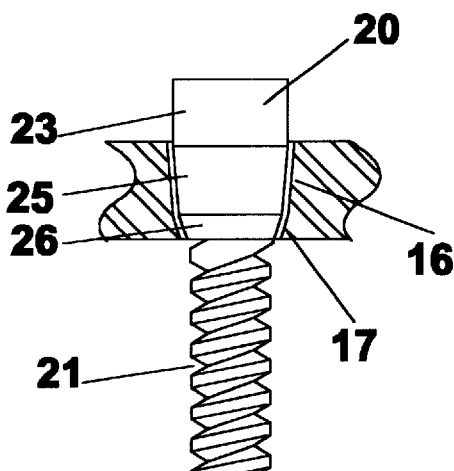
FIG. 6c is a sectional view, at 6—6 of FIG. 5b, of a bone screw with two separate tapered sections each of which has a different angle in the plate.

Referring to FIGS. 5a, 5b, 6a, 6b, and 6c, in the preferred embodiment, the screw 20 is held in place with two or more locking tapers or tapered sections 16 and 17 in plate 12. The bone screw threads may have a cylindrical major diameter as shown in FIG. 6a or a tapered major diameter. The bone screw may be self-tapping. Bone screws 20 each include a head 23, a threaded portion of the shank 21, and a tapered shank portion 22 between the head 23 and the threaded portion 21. The tapered screw section 22 of head 23 has a minor diameter 26 that exceeds the major diameter of the threads of shank 21 and a major diameter 25 larger than the anterior diameter of the plate hole 16. These diameters allow the bone screws 20 to be inserted, shank first, into any of screw holes 13 from the anterior side 11 of plate 12, with the threaded shank 21 passing through the hole 13 of the posterior surface. The thread engages a predrilled and pre-threaded hole 33 in the vertebra 31 and 32 or the graft 30. The bone screw maintains the plate 12 in contact with the vertebra 31 and 32.

The bone screw may also have two or more tapers or tapered sections 25 and 26 as shown in FIGS. 6b and 6c or inserts on the shank of the screw 20. The tapered sections will reduce the tendency of screw head to pivot within the plate. The head of the bone screw includes a means 24, which will accept a driving tool. The driving tool advances the bone screw head into the tapered section to a low profile such that it does not impinge upon the esophagus.

The Graft

After removing the disc and the cartilage, a graft 30, preferably a non-degrading bone growth-compatible material, is positioned between the two vertebrae 31 and 32 in the intervertebral space. Such grafts are structurally load-bearing devices, capable of withstanding the compressive forces supported by the adjacent superior vertebra 31, however they will not resist tensile force experienced at the vertebral to graft interface. The stabilizer system 10 and the surrounding ligaments, tendons, and muscles must be pre-loaded to maintain compression between the graft and the adjacent vertebra during any upper body motion which tends to put the spinal column in tension. The graft 30 must be in compressive contact with the vertebral 31 and 32 ends. The graft 30 also may be metal nonmetal, polymeric, allograft, autograft, or synthetic materials.

The Method

The following is the preferred method for implanting the Spinal Stabilization System 10 of this patent. This is not to imply that it is the only method in which the stabilizing system can be implanted.

1. The disc is removed by means of a commercial tissue remover.
2. The vertebral protrusion 28 is removed if necessary.
3. The graft 30 is forced into position at the center of the vertebral surfaces on 31 and 32. Replacing damaged discs with rigid grafts is well known to those practiced in the art. The method of stabilizing the graft and maintaining the relationship between the two vertebrae is still a changing technology.
4. The plate 12 is selected and the posterior side is placed upon the anterior side 29 of the patient's vertebra 31 and 32.
5. The posterior side of the plate may be positioned temporarily on the vertebra 31 and 32 near the area where it will be attached and repositioned to determine the best location for the screws.
6. Bushings 41, shown in FIG. 8, are inserted into the tapered holes 13 to align the drill and thread tap and to protect the tapered hole.
7. The plate 12, with a guide bushing 41, is used as a template to guide the drill and tap at the position and angle of the matching screw holes.
8. The bone screw holes 33 are drilled and threaded into the vertebrae.
9. The screws 20 are threaded into the remaining holes.

On frequently used plate sizes a metal template may be used in place of the plate 12 to align the drill and tap.

We claim:

1. A stabilizing plate system, for the purpose of fixing one bone segment with respect to one or more other bone segments, or implant of graft material within a bone column, said system comprising;
    (a) a plate member for fixation to individual bone segments having a posterior side for positioning on the bone segments said plate having a plurality of attachment holes for receiving bone screws, and
    (b) a plurality of bone screws configured to engage said plate, and to engage the bone segments for the purpose of retaining said plate to said bone segments, and
    (c) said bone screws having a shank portion, a threaded portion and a head portion, the shank portion having at least one plate contacting surface, and the plate having at least one screw contacting surface, wherein the shank portion is configured and sized such that when the screw is tightened, the at least one plate contacting surface of the shank portion is affixed to the plate by an interference fit, wherein one or both contacting surfaces on the shank or plate yield to create an amount of normal compression forces between these surfaces so as to provide frictional force to retain the contacting surfaces in secure engagement under axial or rotational loading.

2. The stabilizing system of claim 1, wherein the threaded portion of the bone screws engages threads in machined holes within the bone segments.

3. The stabilizing system of claim 1, wherein said interference fit between said bone screws and said plate is provided by at least one locking taper which will prevent screw backout.

4. The stabilizing system of claim 3, wherein the at least one locking taper is angled up to 5 degrees.

5. The stabilizing system of claim 1, wherein the plate holes and bone screws have at least two tapered contacting surfaces corresponding to one another to provide the interference fit therebetween.

6. The stabilizing system of claim 5, wherein the at least two locking tapers are at differing angles.

7. The stabilizing system of claim 1, wherein the interference fit portion of the said screw shank portion extends over at least 1 mm of said plate.

8. The stabilizing system of claim 1, wherein said screws are fixed to said plate and the bone segments with an adhesive-type bonding material.

9. The stabilizing system of claim 1, wherein the shank portion includes a tapered shank portion between the head and the threaded portion.

10. The stabilizing system of claim 1, whereas said plate has at least two locking tapered sections, wherein the at least two locking tapered sections have differing taper angles.

11. The stabilizing system of claim 10, wherein the at least two locking tapered sections extend the full thickness of the plate, such that the full thickness of the plate provides a bending reaction area when engaged with a screw.

12. The stabilizing system of claim 10, wherein the at least two locking tapered sections are configured to provide substantially the widest moment reaction distance and substantially the highest bearing compression stress between the plate and screw.

13. The stabilizing system of claim 1, wherein the plurality of screws are engaged at a designated axial or radial angle relative to the plate to selectively cause pulling of the bone segments together or to provide additional pull out resistance respectively.

14. The stabilizing system of claim 1, wherein said plate is formed with inserts in the holes, the inserts forming the at least one contacting surface and having material characteristics to yield an amount to create said normal compression forces between the contacting surfaces so as to provide frictional force to retain the contacting surfaces in secure engagement under axial or rotational loading.

15. The stabilizing system of claim 14, wherein a plurality of inserts form at least two tapered sections serving as contacting surfaces for engaging the contacting surfaces of the screws.

16. The stabilizing system of claim 1, wherein the shank of the screws extends through a hole to extend beyond the posterior side of the plate, wherein the portion extending beyond the plate has at least one tapered section thereon before the threaded section.

* * * * *